(12) United States Patent
Patel (10) Patent No.: US 7,766,050 B2
(45) Date of Patent: Aug. 3, 2010

(54) CONDUIT AND METHOD OF FORMING

(75) Inventor: Bhavna Patel, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 102 days.

(21) Appl. No.: 10/996,821

(22) Filed: Nov. 24, 2004

(65) Prior Publication Data

US 2005/0152733 A1   Jul. 14, 2005

(30) Foreign Application Priority Data

Nov. 28, 2003   (NZ) ..................... 529893

(51) Int. Cl.
*F16L 11/00* (2006.01)
(52) U.S. Cl. .................. 138/129; 138/148; 138/150; 138/154
(58) Field of Classification Search ............... 138/129, 138/136, 148, 150, 154
See application file for complete search history.

(56) References Cited

U.S. PATENT DOCUMENTS

| | | | | |
|---|---|---|---|---|
| 2,874,722 | A * | 2/1959 | Hamblin | 138/134 |
| 3,073,353 | A * | 1/1963 | Rittenhouse | 138/148 |
| 3,117,596 | A * | 1/1964 | Kahn | 138/122 |
| 3,255,780 | A | 6/1966 | Squirrell | |
| 3,479,670 | A * | 11/1969 | Medell | 623/1.33 |
| 3,495,628 | A * | 2/1970 | Boender | 138/114 |
| 3,674,056 | A * | 7/1972 | D'Aprile | 138/134 |
| 3,739,815 | A | 6/1973 | Rejeski | |
| 3,916,953 | A * | 11/1975 | Nagayoshi et al. | 138/129 |
| 4,129,152 | A * | 12/1978 | Davis | 138/154 |
| 4,196,755 | A | 4/1980 | Kutnyak et al. | |
| 4,204,562 | A | 5/1980 | Kelly | |
| 4,209,043 | A * | 6/1980 | Menzel | 138/154 |
| 4,304,266 | A | 12/1981 | Kutnyak et al. | |
| 4,531,551 | A * | 7/1985 | Eichelberger et al. | 138/129 |
| 5,394,904 | A * | 3/1995 | Winter et al. | 138/137 |
| 5,526,849 | A * | 6/1996 | Gray | 138/133 |
| 5,806,567 | A * | 9/1998 | Fukui et al. | 138/132 |
| 5,848,223 | A | 12/1998 | Carlson | |
| 5,954,096 | A * | 9/1999 | Lepoutre | 138/129 |
| 6,152,186 | A * | 11/2000 | Arney et al. | 138/129 |
| 6,158,477 | A | 12/2000 | Waters | |
| 6,190,480 | B1 | 2/2001 | Carlson | |
| 6,219,490 | B1 | 4/2001 | Gibertoni et al. | |
| 6,237,642 | B1 * | 5/2001 | Lepoutre | 138/129 |
| 6,347,646 | B2 | 2/2002 | Fukui et al. | |
| 6,374,864 | B1 | 4/2002 | Philp | |
| 6,488,052 | B2 * | 12/2002 | Hupertz et al. | 138/135 |

(Continued)

FOREIGN PATENT DOCUMENTS

DE   198 48 172   4/2000

(Continued)

*Primary Examiner*—James F Hook
(74) *Attorney, Agent, or Firm*—Trexler, Bushnell, Giangiorgi, Blackstone & Marr, Ltd.

(57) ABSTRACT

A method of forming a double film layered continuous conduit is disclosed. The method includes applying at least one film of ribbon spirally around a former where at least half of each turn of ribbon overlaps the next turn of the ribbon, such that the leading and trailing edges overlap. A bead of molten plastic is then applied between the overlap.

20 Claims, 5 Drawing Sheets

U.S. PATENT DOCUMENTS

| | | | |
|---|---|---|---|
| 2002/0148522 A1* | 10/2002 | Hupertz et al. | 138/135 |
| 2004/0079371 A1* | 4/2004 | Gray | 128/204.17 |
| 2004/0081784 A1* | 4/2004 | Smith et al. | 428/36.9 |
| 2006/0165829 A1* | 7/2006 | Smith et al. | 425/113 |

FOREIGN PATENT DOCUMENTS

| | | |
|---|---|---|
| EP | 0 814 291 | 12/1997 |
| GB | 974670 | 11/1964 |
| JP | 55-61432 | 5/1980 |

\* cited by examiner

CONDUIT AND METHOD OF FORMING

BACKGROUND TO THE INVENTION

1. Field of the Invention

The present invention relates to components for breathing circuits and in particular to conduits for use in the limbs of breathing circuits. The invention also relates to methods of manufacturing such conduits.

2. Summary of the Prior Art

Figure 1:
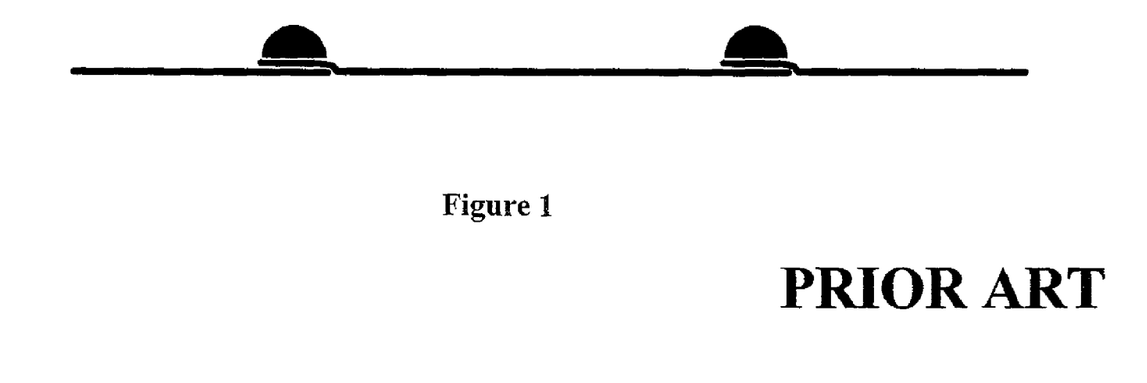
FIG. 1 is a cross sectional side elevation of a conduit according to an embodiment of the prior art.

In assisted breathing, particularly in medical applications, gases are supplied and returned through conduits. Such conduits are ideally light and flexible to ensure the greatest level of comfort for the patient. In the prior art, thin walled conduits are known which include helical or annular reinforcing ribs which act to give the conduit better resistance to crushing and pinching, while still allowing the conduit to be light and flexible. An example of one such conduit is shown in FIG. 1.

It is advantageous to manufacture this type of conduit as a continuous process. In the prior art this is achieved by spiral winding of a thin polymer tape onto a former such that the edges of adjacent layers overlap a small amount. A bead of molten polymer is then applied over the top of the overlapping edges welding them together and simultaneously forming the helical reinforcing ribs. A disadvantage with this forming technique is the difficulty welding several adjacent layers. This problem is especially severe when multiple layer conduit walls are to be formed. While combining the application of a molten bead with another secondary thermal welding process or applying the polymer to the former as a still molten plastic does go some way to alleviating this difficulty, these solutions add complexity to the tube former and may be difficult to achieve with very thin walls.

SUMMARY OF THE INVENTION

It is an object of the present invention to provide a conduit, with particular application to the limbs of a breathing circuit, which will at least go some way towards improving on the above or which will at least provide the public and the medical profession with a useful choice, and/or to provide a method of manufacturing a conduit which will at least go some way towards providing the public and manufacturers with a useful choice.

In a first aspect the invention consists in a method of forming a continuous conduit comprising the steps of:

applying at least one preformed film of ribbon, each having leading and trailing lateral edges, spirally around a former, with at least half of each turn of ribbon overlapping the next turn of said ribbon such that the trailing edge of the ribbon overlaps with each successive leading edge of the successive turn of said ribbon, and applying a bead of molten plastic along between the overlap of said ribbon.

Preferably at least one conductive element is applied and encapsulated between said trailing and said leading edges.

Preferably said bead is positioned and feed onto said ribbon and said former at substantially the centre of said ribbon and said leading edge of said next turn of said ribbon.

Alternatively said bead is positioned and feed over said trailing edge of said ribbon in order to bind said trailing edge to the centre of said next turn of said ribbon.

In yet still a further aspect the invention consists in a conduit comprising:

at least one thin plastic ribbon having a leading and a trailing lateral edge, said ribbon arranged helically with its face substantially parallel with the helix axis, and, apart from at its ends, the trailing edge of each turn of ribbon overlapping the leading edge of a previous turn, a plastic reinforcing bead disposed between each overlapping trailing and leading edge.

Preferably said at least one conductive element encapsulated between said trailing and leading edges.

Preferably said ribbon is at least twice the width of the pitch of said conduit.

Preferably an air gap is formed between the overlapping turns of said ribbon.

Preferably said bead is substantially semicircular in shape.

In one embodiment said ribbon may be a non-breathable plastic material.

In another embodiment said ribbon may be a breathable plastic material.

DETAILED DESCRIPTION OF THE PRIOR ART

The present invention relates to breathing conduits in general and in particular to improved methods of forming thin film spiral wound conduits. Consequently the present invention finds application in breathing conduits fabricated from a variety of materials which may include breathable and/or non-breathable materials (breathable materials being capable of transmitting water vapour). In particular, the present invention targeted at a double layer conduit and the method of forming such a conduit.

Continuous Positive Airway Pressure (CPAP) systems or positive pressure ventilation systems that provide patients suffering from obstructive sleep apnea (OSA) with positive pressure gases often use conduits similar to the prior art described. Often in these applications and in other medical applications, such as with assisted breathing, gases having high levels of relative humidity are supplied to patients and sometimes returned through conduits of a relatively restricted size. The aim of the present invention is to provide an alternative conduit that will withstand the stresses of high use, which is flexible, yet not prone to breakage under axial stretching or movement.

The preferred conduits of the present invention are formed from a non-breathable material, such as a polymer plastic block formed into a homogeneous flat film. An example of such a film is sold under the brand EVOLUE.

In alternative forms of the conduit of the present invention a conduit may be formed from a breathable material, such as a hydrophilic polyester block copolymer formed into a homogeneous flat film. An example of such a film is sold under the brand SYMPATEX.

The following embodiments will be described with particular reference to non-breathable thin film wall construction from materials such as EVOLUE. It will be appreciated however, that in the following described embodiments the material used to form the conduit walls may be either breathable or non-breathable and may also include combinations of both breathable and non-breathable materials. It will also be appreciated by those skilled in the art that the materials supplied to a former used in the manufacture of the conduit may require guides and/or rollers in order to position the film accurately and provide the necessary tension.

It is preferred that the conduit is manufactured from a plastic film of ribbon having a relatively low thickness, so much so that the conduit wall may be insufficiently sturdy to be self supporting. Spiral or helical reinforcing members are therefore provided as part of the tubular wall membrane to provide support. The helical or spiral supporting members are formed from polymer plastic materials and may be of the same material used in the wall of the conduit or any other compatible plastics material.

Conduit Forming

A conduit that is formed using the preformed film of ribbon as described above will now be described. To manufacture a heated conduit a preformed film is preferably used and an electrical wire may be threaded onto the film, such that it is encapsulated in the tube once would to allow for heating of the tube in use.

Figures 2, 3, 4, 5:
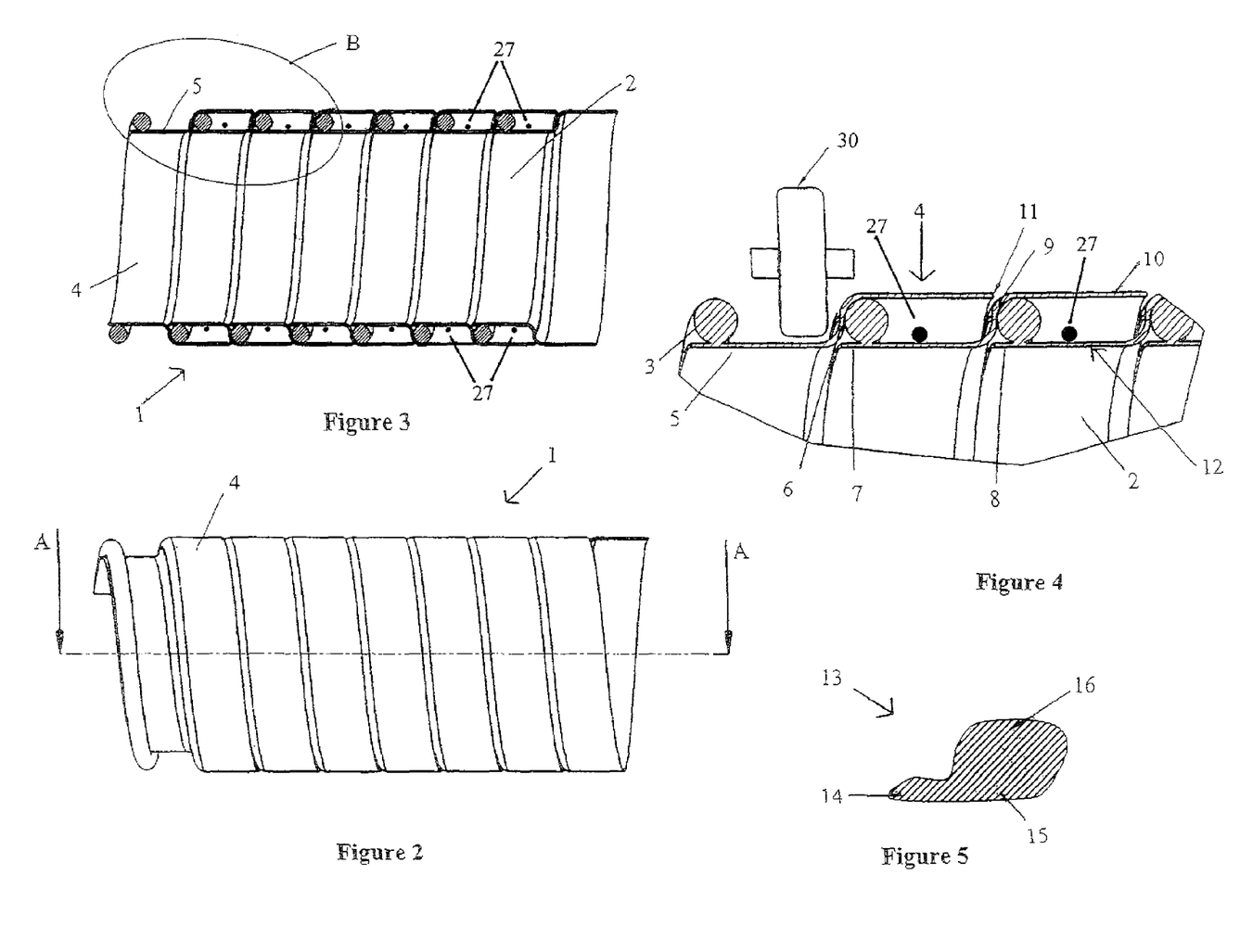
FIG. 2 is a side view of a section of a conduit according to a first embodiment of the present invention.
FIG. 3 is a cross sectional view of a section of the first embodiment of the conduit of FIG. 2 through AA.
FIG. 4 is a cross sectional view of detail B of the conduit of FIG. 3.
FIG. 5 is a cross section of an alternative bead that may be used in the manufacture of a conduit according to the present invention.

FIGS. 2 to 4 illustrate a conduit 1 formed from a film as described above and using the conduit forming method as described below. The conduit may be used as a transport path supplying gases to a patient and has a thin film flexible wall. The film 4, such as the preformed film described above, is arranged in a spiral or helix such that each turn of the film overlaps to form a double wall 2 of the conduit or tube 1. A bead 3 of polymer material is preferably extruded between the overlapping portions of adjacent winds of film to bond the overlapping portions of film to form a continuous conduit or tube 1. The film is preferably at least twice the width of the pitch of the final conduit thus formed, and so a double layer conduit is formed. With the addition of a bead 3, an air gap is formed between consecutive layers, in which various forms of wiring 27 can be wound. This wiring 27 could be a heating element, a sensor element or data wiring. Furthermore, Positive Temperature Coefficient (PTC) material could be used in the place of heating wire.

The overlapping of the film can best be seen in FIG. 4. FIG. 4 shows a cross section of a conduit or tube 1 in detail. A film is threaded onto a rotating mandrel (not shown in FIGS. 2 to 4, but see FIG. 10; mandrel 24). A molten bead 3 is extruded over the edge 5 of the first wind 5 of the film 4 and on the next rotation of the mandrel the centre 6 (or near to centre) of the film 4 is laid over the molten bead 3 as the bead 3 is laid onto the edge 7 of the second wind of film 4. Then on the next rotation the bead 3 is laid onto the next edge 8 of the film 4 and the centre 9 of the second wind 10 of the film is laid over the bead 3. At this point the trailing edge 11 of the first wind 4 of film meets with the centre 9 of the second wind 10 of film and welded to the centre 9 of the second wind 10 of film. Therefore, the molten bead 3 bonds the centre 9 of the second wind 10 of film to the trailing edge 11 of the first wind 4 of film and as the edge 3 of the third wind 12 of the film is beneath the bead 3, these are all bonded together. As the bead dries a continuous conduit is formed. With consecutive turns of the rotating mandrel 24 and film 2 a tube is formed along it that has smooth inner walls.

Additionally a heated roller 30 may be used with the mandrel to assist in the centre of the film to bond with the bead and leading edge of the next turn of film, for example, see FIG. 4. Further, using such a roller 30 would assist in flattening the film layers against the mandrel, resulting in the inner wall of the conduit being smooth.

Further additional heat, in the form of a heated stream of air, heat gun or the like, may be applied to the centre area of the film as it is laid over the molten bead to assist welding of the trailing edge of the film to the centre of the film. Adding additional beat to the process would also assist in the inner wall of the conduit being smooth.

Figure 6:
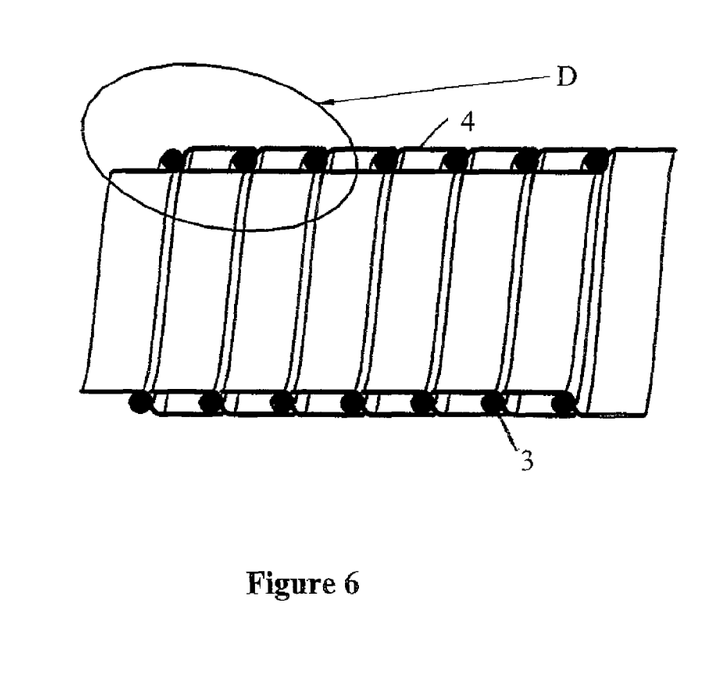
FIG. 6 is a cross section of a second embodiment of the conduit of the present invention.
Figure 7:
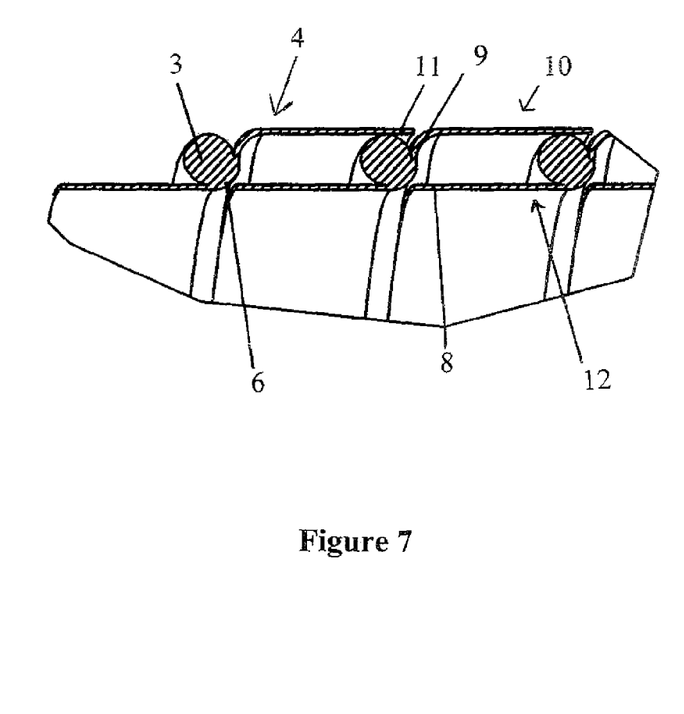
FIG. 7 is a close up view of detail D of the conduit of FIG. 6.

Ideally the bead is positioned and feed onto the film and mandrel as described above as the conduit is formed, that is, between the centre of the film and leading edge of the previous turn of film. Alternatively, the bead could be easily laid over the trailing edge of the film to bind the trailing edge of the first turn of film to the centre of the second third of film and leading edge of the third turn of film. Furthermore, as shown in FIGS. 6 and 7, in yet other forms the bead could be laid in the centre 6 of the first wind 4 of the film, not on the leading edge of the film. Therefore, on the next rotation of the mandrel 24 the heat from the molten bead 3 would bond the trailing edge 11; centre 9 of the next wind 10 of the film and leading edge 8 of the third wind 12 of film.

Preferably the bead is circular in cross section as shown in the appended figures but in other forms the bead could be of a shape that is a specific cross-section that controls the vertical position of the film. For example, in FIG. 5 the bead 13 has an irregular shape having an elongated protrusion 14 extending out from lower side 15 of the main substantially rectangular body 16 of the bead 13.

Figure 8:
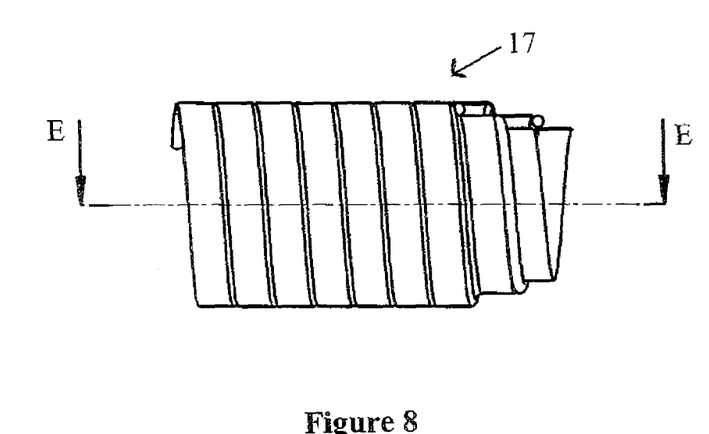
FIG. 8 is a side view of a second embodiment of the present invention where the conduit is made of multiple layers.
Figure 9:
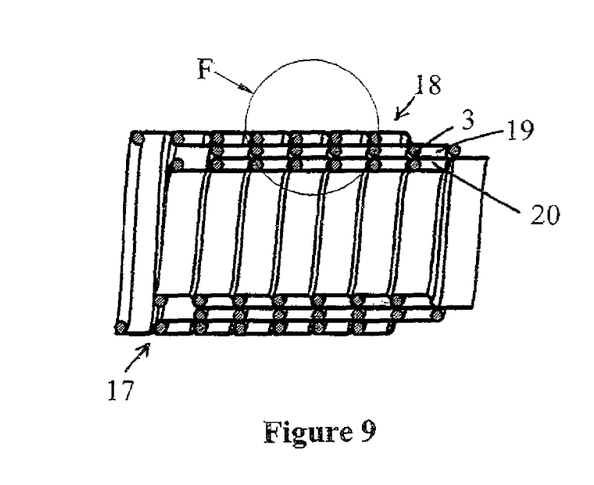
FIG. 9 is a cross section of the conduit of FIG. 8 through EE.
Figure 10:
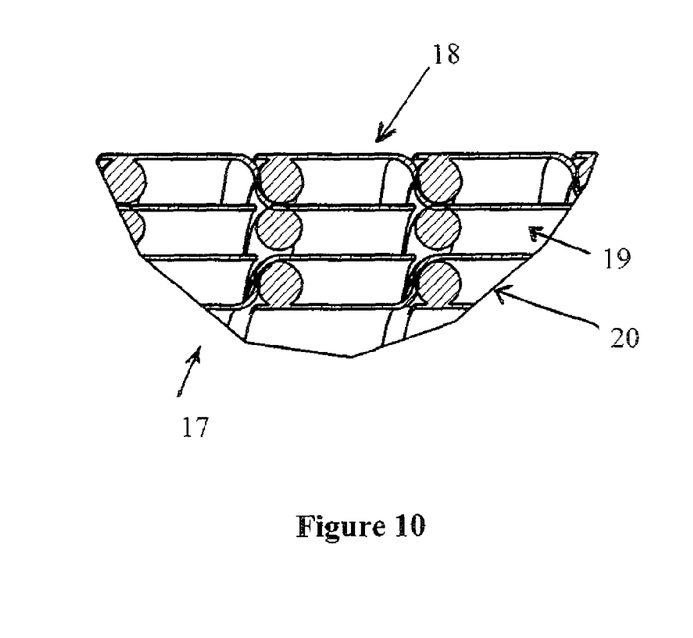
FIG. 10 is a close up view of detail F of the conduit of FIG. 9.

FIGS. 8 to 10 show a multiple layer conduit 17. In this form the apparatus producing the conduit would be similar to that shown in FIG. 10, but would comprise several extruders and spools of film being fed consecutively onto a rotating mandrel. The conduit 17 shown in FIGS. 7 to 9 has three layers 18, 19, 20.

Figure 11:
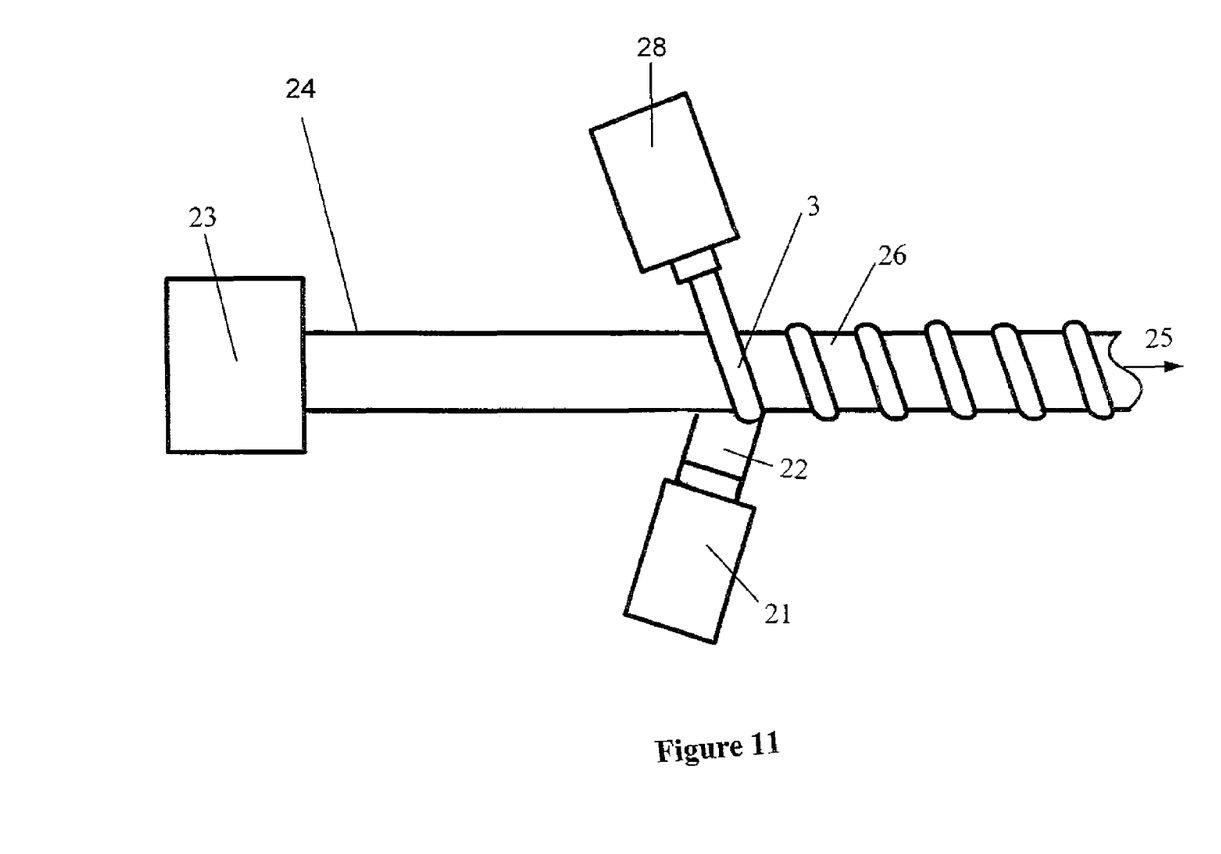
FIG. 11 is a plan view of a conduit forming device for forming any of the embodiments of the conduit of the present invention described herein.

An example of the forming apparatus suitable for manufacturing the conduits of FIG. 2, 6 or 8 is shown in FIG. 11. A spool 21 of preformed film as described above is mounted onto a frame (not shown) of the conduit forming apparatus. The film 22 is drawn from the spool 21 and fed onto a mandrel 24.

The mandrel 24 includes a former, preferably of a known type, including a plurality of rotating rods or cables arranged around a central support rod. The rods or cables extend from and are rotated by a gearbox within a machine stock 26. At least in the conduit forming region the rotating rods follow a helical path. The pitch angle of the rods relative to the support rod controls the pitch angle of the conduit being formed. An example of such a mandrel is a spiral pipeline mandrel available from OLMAS SRL of Italy.

The conduit being formed on the former is rotated and advanced in the direction of arrow 25 by the movement of the rotating cables. The advance speed of the former is selected relative to the rotational speed of the cables and is dependent on the pitch of the helical laying of the film on to the former, such that adjacent turns of the film narrowly overlap. The spool 21 of preformed film 22 as described above is fed onto the former (mandrel 24) in a helical fashion by action of the former. The helical deposition of film 22 forms the wall 26 of the conduit. An extruder 28 extrudes the bead 3 of polymer material onto the overlap of the film 20 winds. The rotating mandrel 24 draws the molten bead 3 over the overlapping portions of adjacent winds of film 20 and is sufficiently heated to weld to the layers of film 20. In the preferred embodiment of the present invention the bead 3 is extruded at a temperature higher than the melting point of the film being used so as to provide enough heat to thermally bond the layers of film together.

In the preferred form the mandrel 24 has air or water cooling to cool the conduit as it is formed on the mandrel 24 and to ensure that the bead 3 does not melt through both the turns of film 20. As the bead 3 is extremely hot when it is extruded onto the film 20, air cooling is required, both internal and external to the conduit being formed, to prevent the film from being melted and/or damaged. The internal air cooling is provided by having hypodermic stainless steel tubing on the mandrel, which sprays several fine jets of air onto the inside of the tube. The external air-cooling is provided by a series of air knives that spray a blade of air onto the outside of the tubing.

The mandrel 24 will now be described in more detail. The mandrel 24 has six stainless steel speedometer cables, all of which are rotated at the same speed. The speedometer cables are located in the mandrel 24 within undercut grooves, which have been machined into the stainless steel mandrel in a helix with a specified angle. The mandrel 24, preferably made of stainless steel, has scallops machined into it between the speedometer cable grooves to provide a clearance so that the film 20 rests on the speedometer cables, rather than the mandrel 24. A groove is also machined into the centre of these scallops to provide a space to place tubing for internal air cooling. The stainless steel mandrel may also be water cooled with monitoring of the water flow rate, to ensure that there is sufficient cooling.

The speedometer cables provide the drive to pull the film 20 onto the mandrel 24 as described above. The helical angle of these cables is important to create the correct amount of overlap of the film 20. The angle of the cables is set at a particular angle to the horizontal such that the film 20 is drawn onto the mandrel 24 and is wrapped around it in a helix as described above. The amount of overlap of the turns of film is critical, because if the overlap is too much or too little then the trailing or leading edges of the film will not be bonded creating loose edges inside or outside the formed conduit wall 26, which can result in non-continuous walls and is likely to cause a reduction in the performance of the conduit.

In other forms of the method of forming a conduit of the present invention more than one film or a thicker film could be used in the formation of the conduit in order to increase the thickness of the conduit wall and thus the walls strength, yet still providing a conduit that is flexible.

If a conduit is produced including a heating wire threaded into one of the gaps produced between the film turns, by feeding the wire onto the film and mandrel during manufacture of the conduit, then such a conduit may reduce the build up of condensation in the conduit and may also offer a means to maintaining the temperature of humidified gases flowing through the conduit. Heated conduits are used as gases transportation pathways in applications such as for Continuous Positive Airway Pressure (CPAP) therapy. In such conduits where the pathway includes conductive wires to heat gases flowing through the pathway, the corresponding connectors, at least at one end of the conduit, will include an electrical connection suitable for connection with the humidified gases source in order to supply electrical energy to the conduit heater wires.

The invention claimed is:

1. A conduit comprising:
   a thin plastic ribbon having a consistent thickness over both length and width, said ribbon helically wound and contorted so that consecutive turns of the ribbon overlap, each turn of the ribbon partially overlapping a previous turn of the ribbon, a trailing lateral edge of each turn of the ribbon bonding with the previous turn of the ribbon at or near a centerline, the overlapping portions of the ribbon separated by an air gap, and
   a separate plastic reinforcing bead bonding consecutive turns of the ribbon together to form the conduit, each turn of the ribbon contacting two consecutive turns of the reinforcing bead, a first turn of said two consecutive turns of the reinforcing bead bonding with each turn of the ribbon at an inner face near the centerline and a second turn of said two consecutive turns of the reinforcing bead bonding with each turn of the ribbon at an outer face near a leading lateral edge.

2. A conduit as claimed in claim 1 wherein each turn of the ribbon bends around the first turn of the reinforcing bead to form consecutive layers of the conduit wall, each turn of the ribbon substantially conforming to the bead contour at an interface between the ribbon and the bead.

3. A conduit as claimed in claim 1 wherein the first turn of the reinforcing bead bonds to the previous turn of the ribbon at an outer face near a trailing lateral edge.

4. A conduit as claimed in claim 1 wherein each turn of the ribbon underlaps a subsequent turn of the ribbon, the subsequent turn of the ribbon bonding with an outer face of each turn of the ribbon near the first turn of the reinforcing bead.

5. A conduit as claimed in claim 1 wherein the second turn of the reinforcing bead bonds with a subsequent turn of the ribbon at an inner face near a centerline.

6. A conduit comprising:
   a thin plastic ribbon having a consistent thickness over both length and width, said ribbon helically wound and contorted so that consecutive turns of the ribbon overlap, each turn of the ribbon partially overlapping a previous turn of the ribbon, a leading lateral edge of each turn of the ribbon bonding with the subsequent turn of the ribbon at or near a centerline, the overlapping portions of the ribbon separated by an air gap, and
   a separate plastic reinforcing bead bonding consecutive turns of the ribbon together to form the conduit, each turn of the ribbon contacting two consecutive turns of the reinforcing bead, a first turn of said two consecutive turns of the reinforcing bead bonding with each turn of the ribbon at an outer face near the centerline and a second turn of said two consecutive turns of the reinforcing bead bonding with each turn of the ribbon at an inner face near a trailing lateral edge.

7. A conduit as claimed in claim 6 wherein each turn of the ribbon bends around the first turn of the reinforcing bead to form consecutive layers of the conduit wall, each turn of the ribbon substantially conforming to the bead contour at an interface between the ribbon and the bead.

8. A conduit as claimed in claim 6 wherein the first turn of the reinforcing bead bonds to the subsequent turn of the ribbon at an inner face near a trailing lateral edge.

9. A conduit as claimed in claim 6 wherein each turn of the ribbon overlaps a previous turn of the ribbon, the previous turn of the ribbon bonding with an inner face of each turn of the ribbon near the first turn of the reinforcing bead.

10. A conduit as claimed in claim 6 wherein the second turn of the reinforcing bead bonds with a previous turn of the ribbon at an outer face near a centerline.

11. A conduit comprising:
a thin plastic ribbon having a consistent thickness over both length and width, said ribbon helically wound and contorted so that consecutive turns of the ribbon overlap to form consecutive layers of the conduit wall, a first and second lateral edge of each turn of the ribbon separated both along and transverse to a longitudinal axis of the conduit, and
a separate plastic reinforcing bead bonding consecutive turns of the ribbon together to form the conduit, the reinforcing bead bonding with each turn of the ribbon at or near a centerline, each turn of the ribbon bonding with two consecutive turns of the reinforcing bead, the reinforcing bead separating the consecutive layers of the conduit wall to form an air gap.

12. A conduit as claimed in claim 11 wherein each turn of the ribbon bends around a first turn of said two consecutive turns of the reinforcing bead to form underlapping and overlapping portions with adjacent turns of the ribbon,
a second turn of said two consecutive turns of the reinforcing bead bonding with each turn of the ribbon near the first lateral edge,
the second lateral edge of each turn of the ribbon bonding with an adjacent turn of the ribbon near an adjacent turn of the reinforcing bead.

13. A conduit as claimed in claim 12 wherein the first turn of said two consecutive turns of the reinforcing bead separates the underlapping and overlapping portions of each turn of the ribbon, a first air gap being formed between each turn of the ribbon and a previous turn of the ribbon and a second air gap being formed between each turn of the ribbon and the subsequent turn of the ribbon.

14. A conduit as claimed in claim 11 wherein each turn of reinforcing bead bonds with two consecutive turns of the ribbon.

15. A conduit as claimed in claim 14 wherein each turn of the reinforcing bead further bonds with an adjacent turn of the ribbon near a lateral edge.

16. A conduit as claimed in claim 11 wherein a first turn of said two consecutive turns of the reinforcing bead bonds to an outer face of each turn of the ribbon near the centerline and a second turn of said two consecutive turns of the reinforcing bead bonds to an inner face of a same turn of the ribbon near the first lateral edge.

17. A conduit as claimed in claim 11 wherein a first turn of said two consecutive turns of the reinforcing bead bonds to an inner face of each turn of the ribbon near the centerline and a second turn of said two consecutive turns of the reinforcing bead bonds to an outer face of a same turn of the ribbon near the first lateral edge.

18. A conduit as claimed in claim 11 wherein the reinforcing bead has a substantially regular pitch and thickness over the length of the conduit, the first and second lateral edges of each turn of the ribbon separated along the longitudinal axis of the conduit by approximately twice the pitch of the reinforcing bead.

19. A conduit as claimed in claim 11 wherein the reinforcing bead has a substantially regular pitch and thickness over the length of the conduit, the first and second lateral edges of each turn of the ribbon separated transverse to the longitudinal axis of the conduit by approximately the thickness of the reinforcing bead.

20. A conduit as claimed in claim 11 wherein the reinforcing bead has a substantially regular pitch and thickness over the length of the conduit, the pitch of the reinforcing bead being less than the separation between the first and second lateral edges of the thin flat plastic ribbon.

* * * * *